United States Patent [19]
Vapola et al.

[11] Patent Number: 5,584,291
[45] Date of Patent: Dec. 17, 1996

[54] METHOD FOR RECOGNIZING AND IDENTIFYING EMERGENCY SITUATIONS IN AN ANESTHESIA SYSTEM BY MEANS OF A SELF-ORGANIZING MAP

[75] Inventors: Mauri Vapola, Espoo; Pekka Meriläinen, Helsinki, both of Finland

[73] Assignee: Instrumentarium, Oy, Helsinki, Finland

[21] Appl. No.: 217,889

[22] Filed: Mar. 25, 1994

[30] Foreign Application Priority Data

Mar. 26, 1993 [FI] Finland .................................. 931348

[51] Int. Cl.⁶ .................................................. A61B 5/00
[52] U.S. Cl. ........................ 128/630; 128/670; 128/671
[58] Field of Search ................................... 128/630, 633, 128/670, 671

[56] References Cited

U.S. PATENT DOCUMENTS

| | | | |
|---|---|---|---|
| 4,776,339 | 10/1988 | Schreiber | 128/633 |
| 4,823,807 | 4/1989 | Russell et al. | 128/773 |
| 4,883,051 | 11/1989 | Westenskow et al. | 128/204.21 |
| 5,271,411 | 12/1993 | Ripley et al. | 128/702 |

FOREIGN PATENT DOCUMENTS 0465851  1/1992  European Pat. Off. .

OTHER PUBLICATIONS

Leinonen, L, "Journal of Speech and Hearing Research", vol. 35 No. 2 pp. 287–295, Apr. 1992. (Abstract).

Syed, A, Conference Title: Real–Time Systems Symposium, pp. 271–274, 1992, (Abstract).

Tirri, H. 3rd International Conference, FODO 1989 Proceedings pp. 474–488, 1989, (Abstract).

Linkens, D. A., "Non–Linear control for anaesthetic depth using neural networks and regression", Proceedings of the 1992.

IEEE International Symposium on Intelligent Control, pp. 410–415, 1992, (Abstract).

Sittig, D. F. Journal: Computers and Biomedical Research, vol. 25, No. 6, pp. 547–561, 1992, (Abstract).

Wang, L., Journal: Biological Cybernetics, vol. 64, No. 3 pp. 231–241, 1991.

*Primary Examiner*—Angela D. Sykes
*Assistant Examiner*—Stephen D. Huang

[57] ABSTRACT

A method for recognizing and identifying emergency situations in an anesthesia system measures a plurality of variables associated with an anesthesia delivery, the measurement values of said measured variables are formed into pattern vectors characterizing the instantaneous states of the system, the system is trained prior to the actual measurement situation with a reference material comprising pattern vectors corresponding to actual situations, and on the basis of measured pattern vectors corresponding to actual situations, and on the basis of measured pattern vectors and trained material, the emergency situations are recognized and possibly identified. The reference material is trained to the system using self-organizing maps, and the pattern vectors formed from the measurement results are compared with weight vectors ($m_i$) of the self-organizing map to recognize and identify the emergency situations.

5 Claims, 7 Drawing Sheets

METHOD FOR RECOGNIZING AND IDENTIFYING EMERGENCY SITUATIONS IN AN ANESTHESIA SYSTEM BY MEANS OF A SELF-ORGANIZING MAP

FIELD OF THE INVENTION

The invention is related to a method for recognizing and identifying emergency situations in an anesthetic system.

BACKGROUND OF THE INVENTION

Accordingly, the invention disclosed in the present patent application concerns such a method which provides improved patient safety by identifying emergency situations related to an anesthetic system prior to the occurrence of a real accident situation. By virtue of the method, the user can easily recognize the existence of an emergency situation and the origin of such an emergency situation at an earliest possible stage before an actual injury to the patient is caused. In the context of the present patent application, the term "anesthesia system" is used denoting the entity formed by the patient and the equipment connected to the patient during anesthesia.

Risks associated with anesthesia have been assessed in a plurality of investigations, and the results obtained therein have varied according to the patients' age distribution and health condition of the patients, time of the investigation and geographical location of hospitals participating in the investigation. Actually, the only conclusion that can be drawn from the results is that the risks associated with anesthesia today are relatively small. For instance, the summary compiled by Derrington in 1987 on the research results from anesthesia risk assessments revealed the risk associated with anesthesia to be maximally 22 death cases in 10,000 anesthesias (Derrington, M. C., and Smith, G. "A review of studies of anaesthetic risk, morbidity and mortality", *British Journal of Anaesthesia* 59, pp. 815–833, 1987). In most of the investigations, the actual risks were even below this, and for example, according to a study performed in 1986 in Turku, Finland, the corresponding anesthetic risk level in Finland was on the average only approx. 0.61 death cases in 10,000 anesthesias (Tikkanen, J. "Ariestesla-ja leikkaustoimenpiteisiin liittyvat kuolemat Suomen sairaaloissa v. 1986 (title in English: "Death cases associated with anesthetic and surgical operations in Finnish hospitals in 1986"), Doctoral thesis, Turku university, 1992.)

Notwithstanding the low risk level of anesthesias, each patient injury or death caused by anesthesia is excessive. To recognize developing emergency situations and eliminate them earliest possible phase before the occurrence of an injury, the patient status is today supervised by means of values measured and computed by different kinds of monitoring equipment, typically displayed by the monitoring equipment in the form of numerical values or graphs. Some of the most common examples of such monitored variables are blood pressure, ECG, blood oxygen saturation level and numerical values and graphs related to the composition, pressure and flow rate of the gas mixture inspired by the patient. Different patient complications, incorrect use of equipment and actual fault situations of the equipment are then reflected as changes in the values measured and computed by the monitoring equipment.

The wider the spectrum of numerical values and graphs crucial to the recognition of emergency situations made available to the anesthesia personnel, the better the possibilities, at least in theory, of recognizing developing emergency situations. In practice the patient and the anesthesia apparatus during the anesthesia form a very complex and almost inseparable entity. Therefore, it is extremely difficult to deduce the existence of an emergency situation and its cause on the basis of numerous curves and values shown on the monitor screens. While deduction capability increases with personnel training, experience and improved user interfaces, at some point a limit is reached after which the addition of more values and graphs on the displays no longer improves patient safety. Also the almost infinite number of acceptable situations hampers the recognition of emergency situations at their early stage. For example, no ideal set values can be given to an anesthesia unit, but rather, the tidal volume, pressure, gas mixture composition, etc., van according to the patient's weight, age, sex, operating posture, physical condition, type of operation and a great number of other parameters. While measurement results clearly deviating from acceptable values can be easily noticed, the difficulty of identifying the cause of the emergency situation remains.

The occurrence of an emergency situation is facilitated by upper and lower limit alarms, which today are programmed in most anesthesia monitoring equipment. Such upper and lower alarm limits are defined for each variable measured or computed by the equipment from the measurement values, and when the measured values fail to stay between the set alarm limits, the monitoring equipment issues an alarm. If the upper and lower alarm limits are set very close to each other, most of the issued alarms are false. Though the use of tightly set alarm limits may in principle permit the recognition of a developing emergency situation at a relatively early stage, the great number of false alarms tends to prevent the identification of emergency situations in practice. Annoyed by such false alarms, the personnel often resorts to indeed entirely disabling the alarms (Kerr, J. H. "Warning devices", *British Journal of Anaesthesia*, 57, pp. 696–708, 1985).

Accordingly, the problems of false alarms are solved in a great number of conventional monitoring equipment by defining the default values of alarm limits so wide that false alarms are practically nonexistent with the exception of the start and end phases of anesthesia. If the measured values, however, ultimately violate the upper or lower alarm limit, the patient may in the worst case have already been subjected to an injury, and even in the most favorable cases, the time remaining to salvage the patient may be extremely marginal. In such a situation it is of invaluable importance that the anesthesia personnel can rapidly identify the cause of the emergency situation. Such cause of the emergency situation is not identified by the limit alarms, which rather only provide information on which variable(s) has/have violated the set alarm limit(s).

Construction of more intelligent systems capable of identifying emergency situations has been attempted by way of evaluating the measurement values with analytical means, and then using the found correlations to develop simple rule-based systems and expert systems (Jiang, A. "The design and development of a knowledge-based ventilatory and respiratory monitoring system", Doctoral thesis, Graduate School of Vanderbilt University, 1991; and Nederstigt, J. A. "Design and implementation of second prototype of the intelligent alarm system in anesthesia", Diploma Engineer's (M.Sc.) thesis, Eindhoven University of Technology, 1991), while also these systems require an explicit definition of the variable values used in the identification process. However, the number of measured variables is large, and the correlations between the variables are difficult to establish, further complicated by the arbitrariness of judgment between a normal and an abnormal situation. Moreover, the identification of emergency situations is hampered by the different behavior of the measured variables at different operating points of the anesthesia unit. The term "operating point" is used herein denoting such a pattern vector which corresponds to the normal situation with, e.g., predefined anesthesia unit settings and predefined patient. Not even expert systems are particularly well suited to handling such slightly fuzzy relationships, causing them to grow to extremely complicated dimensions with a slow response and rather massive structure.

Westenskow has in his patent application (titled "Device and method for neural network breathing alarm", Westenskow, D., Salt Lake City, filed under patent application no. PCT/US90/05250, 14.9.1990(4.4.1991), 44 pp.) tried to solve the above-described problems by way of an artificial neural network based on error backpropagation. Conventionally, the term "artificial neural network" is used to denote networks formed by parallel cells in which a great number of functionally simple cells are connected to each other. The cells are generally adaptive, or learning, and in a system based on artificial neural networks, the analysis of measurement value changes associated with emergency situations is left to the neural network. Through such a process, the neural network learns to differentiate normal and abnormal situations from each other. Simultaneously, the network learns the mutual relationships of the measured variables in different situations, whereby the cause of the emergency situation is identified in addition to the recognition of the emergency situation.

Artificial neural networks are particularly suited to different kinds of pattern recognition tasks. Thus, they have been successfully used in, e.g., speech recognition, handwritten text recognition, texture recognition and robotics. Pattern recognition by means of artificial neural networks has in the prior art also been tested in different kinds of operating condition monitoring tasks to which both the method of Westenskow and the method disclosed in this patent application basically belong: differently from industrial processes, in anesthesia man simply replaces one of the components in the system being monitored.

In the recognition of emergency situations associated with anesthesia, the measurement results are processed into pattern vectors which the artificial neural network then classifies as either a normal situation or an emergency situation with simultaneous identification of the cause of the emergency situation. The different components of the pattern vector are later denoted as "features". The pattern vectors associated with different emergency situations are taught to the neural network prior to the actual identification process, and to obtain sample situations used for training the system, Westenskow has used both a respiration simulator and test animals. During the collection of the sample situations, the emergency situations to be identified are repeated as many times and with as many settings of the anesthesia unit as possible. The features computed from the measurement results obtained from emergency situations are taught to the neural network through a separate learning process. Then, the neural network learns to identify also such pattern vectors which differ from the initial training vectors taught to the neural network, while still bearing a similarity, thus permitting the neural networks during the identification of emergency situations to perform a generalization from the samples taught to the system. Thus, the above-discussed learning process which is also described in Westenskow's patent application is by no means novel: a corresponding process is carried out when any neural network is used in any possible application.

The cause of an emergency situation is identified according to Westenskow's patent application by comparing the measurement value of a given instant of time to the value obtained during the preceding measurement session, whereby the dependence of the features used for identification on, e.g., the settings of the anesthesia unit is reduced. However, changes in the anesthesia unit settings and normal physiological changes in the patient cause false alarms in a system based on recognition of changes, while hazardous changes which proceed gradually remain unrecognized. To remove such false alarms, Westenskow presents in his patent application a solution in which the presence of an emergency situation is first recognized by means of an error backpropagation neural network, and only when such an emergency situation is recognized, the cause of the emergency situation is identified by means of another, similar type of neural network.

However, the invention disclosed by Westenskow has several drawbacks, most of which are related to the type of neural network employed. A discussion of the drawbacks associated with the solution is given below:

1. Determination of uncertainty level for the identification result is not reliable by means of a backpropagation neural network in the case where the pattern vector to be identified fails to resemble any of the training vectors taught to the neural network. Then, an entirely incorrect identification result may plausibly have even more hazardous consequences than a message reporting that identification is most probably not possible at all.

2. As measurement results from both normal situations and emergency situations must be used in the training of the neural network used for recognizing an emergency situation, training by the user in actual clinical conditions is not possible. Further, the average measurement values obtained during different kinds of operations can vary significantly from each other: For example, higher than normal tidal volumes are used in neurosurgical operations, which further results in a fall of the expiratory air $CO_2$ significantly below the values used in normal anesthesia. The tidal volume and respiration rate employed also vary depending on the patient's size and the preferences of the anesthesiologist.

3. Giving an explanation for the reasons of the identification result to the user is extremely difficult if not even impossible. This inherent property of artificial neural networks is frequently criticized, particularly in conjunction with the identification of emergency situations related to anesthesia. In fact, for a general case a neural network appears as a black box: a pattern vector is taken to the input of the network and the output of the network provides an identification result, while nobody has an exact information on the grounds on which the neural network ended up in the final conclusion, and therefore, also user reservations on the reliability of the conclusion are easily launched.

4. After the measurement results have permanently settled to the level of the emergency situation, identification of the cause of the emergency situation is no longer possible.

5. Identification of causes of gradually developing emergency situations is not possible.

SUMMARY OF THE INVENTION

It is an object of the present invention to overcome the drawbacks of the above-described prior-art technology and to provide an entirely novel method for recognizing and identifying emergency situations occurring in an anesthesia system.

The invention is based on utilizing a self-organizing map in the training and measurement phases of the system.

More specifically, the method in accordance with the invention is characterized by what is stated in the characterizing part of claim 1.

It is a primary object of the method according to the invention to achieve the recognition of emergency situations associated with anesthesia and the identification of the cause of such situations independently of the system operating point and at the earliest possible instant. It is a second object of the present invention, different from that disclosed by Westenskow, to express, besides the recognized emergency situation, the uncertainty level of the identification result. It is a third object of the invention is to recognize the existence of an emergency situation by means of an artificial neural network after the network has been trained by means of samples related to a normal situation alone. It is a fourth object of the invention to express to the user, besides the identification process result, also the grounds for the identification result. A further object is to achieve the identification of gradually developing emergency situations as well as a reliable identification of an emergency situation also after the settling of the measurement results and an elucidated presentation of measurement result trends to the user.

All the above-mentioned objects are achieved by per/brining the identification of both an emergency situation and its cause by using particularly an artificial neural network, called the self-organizing map, developed by Professor Kohonen, as well as modifications of the map and algorithms derived therefrom (Kohonen, T. "The Self-Organizing Map", Proceedings of the IEEE, 78, pp. 1464–1480, 1990, and Kohonen, T. "Self-Organized Formation of Topologically Correct Feature Maps", *Biological Cybernetics,* 43, pp. 59–69, 1982), and by using an adaptive process of emergency situation identification. The self-organizing map possesses general properties resembling those of other neural network types that enable the recognition and identification of emergency situations without requiring an explicit determination of values for the parameters used in the identification process. On the other hand, the self-organizing map has properties capable of overcoming the drawbacks associated with Westenskow's invention discussed above.

With others, Kohonen has described the function of the self-organizing map rather exhaustively in the literature, and the function of the map can be examined using the Public Domain software package SOM_PAK released by the Laboratory of Information Technology, Helsinki University of Technology. In this context, the operating principle of the map is only outlined, and the purpose of the description given below is to elucidate the reasons why the self-organizing map in particular excels in the recognition and identification of emergency situations occurring in an anesthesia system. Probably the most exhaustive presentation of the equations related to the self-organizing map can be found in Kohonen's paper "The Self-Organizing Map" cited above. Descriptions of annexed diagrams given below elucidate both the identification of the pattern vector and the training phase of the map.

Generally, a self-organizing map comprises a set of map cells represented in a one- or two-dimensional space, whereby said cells are located in a given ordered array. In a two-dimensional map said ordered array conventionally refers to a square or hexagonal lattice. Each map cell in the array is assigned a weight vector $m_i$ where the subindex $i$ refers to the location of the cell in the array. For example, in a two-dimensional square map the subindex $i=(x,y)$, where x is the x-coordinate of the cell location and y is the corresponding y-coordinate.

Each weight vector $m_i$ represents a given set of the pattern vectors used for training the map, and accordingly, identification by means of the map simply occurs through finding from the map the weight vector closest matching with the pattern vector to be identified; the map cell thus found is later called the "winner". The dissimilarity distance between the two vectors is most generally computed as the Euclidian distance. The actual identification result is classified on the basis of pattern vectors earlier classified for the winner cell: For example, if the winner cell for the pattern vector to be identified has earlier classified 56 pattern vectors related to emergency situation A and 3 pattern vectors related to emergency situation B, the most likely identification result is declared as emergency situation A.

During the training phase of the self-organizing map, the weight vectors of the map cells gradually change so as to make their locations align according to the density distribution of the pattern vectors in the training material. Thus, if a greater number of pattern vectors in the training material corresponds to, e.g., emergency situation A than to emergency situation B, also the number of map cells representing part A of the map space is greater than that representing pan B of the map.

Also an essential process occurring during the training phase is the ordering process of the map cells which in the present context does not refer to actual movement of the cells on the map, but rather, altering the weight vectors in such a manner that makes the location of each cell on the map correspond in a given manner to the cells weight vector when the weight vector is compared with the weight vectors of the adjacent cells on the map. In practice this means that weight vectors corresponding to cells close to each other on the map according to a given metric are as a rule located closer to each other on the map than the weight vectors of cells farther removed from each other. However, this rule cannot be generalized for all cases: Projection of feature map vectors with a dimensionality higher than two onto a two-dimensional map so as to retain their relative distances is generally impossible. Then, the cells can be considered locally ordered. If both the feature-containing vectors to be identified and the map are one-dimensional, the concept of order must obviously be understood referring to the ordering of weights by their magnitude according to the order of the map cells, while exact order relationships for multidimensional feature vectors and maps cannot be expressed at all.

The self-organizing map is trained unsupervised, that is, an emergency situation associated with a pattern vector is not revealed to the map during the training phase, but rather, the emergency situations associated with the map cells are assessed only after the training phase by testing to which cells of the map the pattern vectors of the training material associated with different emergency situations are classified. As each pattern vector is associated either with a normal situation or some emergency situation, all available information is not utilized during the training phase, which may lead to learning results inferior to those obtained by means of supervised learning process of a backpropagation neural network. However, the identification accuracy of the self-organizing map can be improved through the use of so-called learning vector quantization algorithms (LVQ algorithm), cf. Kohonen, T., Kangas, J., Laaksonen, J., and Torkkola, K. "LVQ_PAK: A Program Package for the Correct Application of Learning Vector Quantization Algorithms", *Proceedings of the International Joint Conference on Neural Networks* (IJCNN), Baltimore, Md., Jun. 7–11, 1992, pp. I-725-I-730, 1992.

The training phase of both the system disclosed in the patent application of Westenskow and that based on the method according to the invention described in the present patent application occurs in the same, conventionally employed manner:

1. Measurement results associated with the classes (emergency situations) to be identified are collected (e.g., by means of a respiration simulator or test animals) and features are computed thereof. The computed features are formed into pattern vectors.

2. The pattern vectors are taught to the neural network until a measure selected to characterize the learning level indicates that a sufficiently good learning result has been attained. For the self-organizing map, a suitable measure of learning level is, e.g., the distance between the pattern vector being taught to the map and the weight vector of the winner cell, whereby a sliding average is computed over a desired time interval. Later in this text this mutual distance between the weight vector of the winner cell and the pattern vector to be identified or being taught is referred to as the "quantization error".

As already mentioned above, when using the map, a further phase after the actual training phase must be performed to test to which cells of the map the pattern vectors of the training material associated with different emergency situations are classified.

To recognize the existence of emergency situations and identify their causes, this invention uses an approach similar to that disclosed in the patent application by Westenskow. Here, the existence of an emergency situation is first recognized, and only after such a recognition of an emergency situation, the cause of the emergency situation is identified. Then, the recognition of an emergency situation is based on so-called absolute features, whereby the emergency situation is recognized using characterizing values computed from the measurement results of a given instant of time alone in the computation of the features. Later in this text the pattern vector formed by the absolute features is referred to as the "absolute pattern vector".

Differently from the invention disclosed by Westenskow, the cause of the emergency situation is identified by comparing the absolute pattern vector of a given instant of time with a reference vector which is not the absolute pattern vector used during the preceding identification computation nor the sliding average of several preceding absolute pattern vectors. In this application the reference vector is formed by first recording a relatively small number (e.g., 5) of absolute pattern vectors associated with normal situations and subsequently computing, e.g., the vector median of the pattern vectors (cf. Astola, J., Haavisto, P., and Neuvo, Y. "Vector Median Filters", *Proceedings of the IEEE*, 78, pp. 678–489, 1990), or the average thereof. A timber possibility is the estimation of the reference vector values from information related to the anesthesia unit and patient posture.

The above-described method enables reliable identification of an emergency situation also after the measurement results have settled to the level corresponding to the emergency situation. Simultaneously, gradually developing emergency situations can be identified.

Differently from the invention disclosed by Westenskow, the existence of an emergency situation is recognized according to the present invention by training the map with samples associated with normal situations alone. To accomplish this, the self-organizing map toms a representation of normal situations, and the existence of an emergency situation is recognized when the quantization error exceeds a discrete limit defined by the user. A similar approach has also been investigated m a Diploma Engineer's (M.Sc.) thesis by Mika Kasslin (Kasslin, M. "Use of self-organizing feature maps in condition monitoring for maintenance", Diploma Engineer's (M.Sc.) thesis, Helsinki University of Technology, 1992). Viktor Tryba and Karl Goser have studied the method m the control of a chemical process (Tryba, V. and Goser, K. "Self-Organizing Feature Maps for Process Control m Chemistry", *Proceedings of the International Conference of Artificial Neural Networks* (ICANN), Espoo, Finland, Jun. 24–28, 1991, Amsterdam, Elsevier Science Publishing Company, pp. 847–852.)

Thus, the user can tram the feature map capable of recognizing the existence of an emergency situation entirely during normal anesthesia and no induced emergency situations are required for attaining a reliable learning result. Moreover, individual maps of emergency recognition with personal preferences can be formed for, e.g., different anesthesiologists and different kinds of patients. Also each type of operation can have an individual type of emergency recognition map. Thus, a method is achieved capable of taking into account average differences related to operating personnel, patients and type of operation, and moreover, recognizing the existence of an emergency situation more reliably than the method provided by Westenskow's invention.

The computed quantization error can also be utilized in the identification of the cause of the emergency situation. The most probable emergency situation related to a given pattern vector is deduced from the emergency situation associated with the winner cell of the map, but if the quantization error between the pattern vector and the winner cell is large, the identification result can be considered uncertain. Thus, the uncertainty level can be expressed simply by visualizing the size of the quantization error. In the invention by Westenskow, the expression of the uncertainty level is not reliable, because the identification process in a backpropagation network is based on hypersurfaces separating the different classes. In case the pattern vector is located far removed from the trained vectors yet, however, properly with respect to the hypersurfaces, the identification result may seem reliable, while in/hot it can be extremely unreliable.

The grounds used by the self-organizing map in the identification process can be simply resolved by examining and visualizing the values of the features in different parts of the map. In this manner it can be deduced which features are effective in the differentiation of a given emergency situation from another emergency situation. Such a deduction is facilitated by the simple structure of the map and the mutual order of the map cells. Finding similar resolving possibilities in the invention by Westenskow is extremely difficult.

The magnitude of measurement results caused by an emergency situation and of feature changes computed from the results may vary widely at different operating points of the anesthesia system. To improve the identification accuracy, the present invention uses a method in which the operating point of the anesthesia system is first identified by means of a map trained with absolute pattern vectors, said being later referred to as the "level 1 map". Each cell in the level 1 map is associated with an assigned level 2 self-organizing map, and correspondingly each level 2 map is associated with at least one cell or level 1 map. Thus, each cell of a level 1 map need not necessarily have an exclusive level 2 map; namely, if the changes caused by, e.g., two different emergency situations resemble each other at operating points mapped in two different cells of the level 1 map, the cause of the emergency situations can be identified by virtue of the same level 2 map. The entity formed by the level 2 self-organizing maps is later in this text referred to as a "map set".

Besides the identification result at a given instant of time, the self-organizing map can also render a highly visual clue on a possible emergency situation in case the identification result would be incorrect for some reason. As the mutually analogous emergency situations are classified close to each other on the self-organizing map, the emergency situations closest probable can be inferred from the emergency situations associated with the neighbor cells of the winner cell or cells. Besides the above-mentioned identification result at a given instant of time, the self-organizing map is capable of visualizing the changes of the measurement results as a function of time by plotting the locus of the winner cell as a dashed line onto the map coordinate system. As the map cells are located in a certain order, the plotting of the broken line occurs without any major jumps. With respect to user-friendliness, the well-behaved mutual order of the map cells gives an additional benefit in this manner. The same property can be utilized to visualize the interaction of trends associated with the singular variables currently in use.

BRIEF DESCRIPTION OF THE DRAWINGS

In the following the method according to the invention and the factors related to the function of the method are described in greater detail with the help of the annexed drawings in which.

DETAILED DESCRIPTION OF THE PREFERRED EMBODIMENTS

Figure 1:
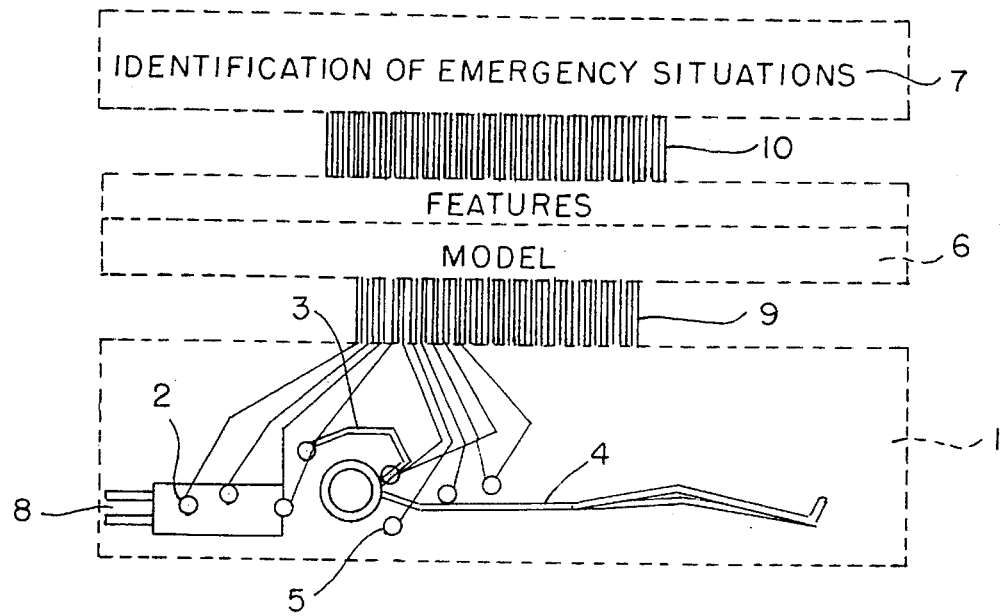
FIG. 1 is a diagrammatic presentation of a method capable of recognizing emergency situations of an anesthesia system in a general case.

FIG. 1 outlines the system for identifying emergency situations in a general anesthesia system. The legend of the reference numerals used in the diagrams is given below:

1 Entity formed by the patient, anesthesia unit, measurement transducers, sampling tubes and other anesthetic accessories
2 Anesthesia unit
3 Breathing circuit of the anesthesia unit
4 Patient
5 Measurement transducer
6 Event model used in the computation of features
7 Identification of emergency situations by means of, e.g., limit alarms, simple rules, expert systems or neural networks
8 Connections to hospital gas system
9 Measurement results
10 Pattern vector The purpose of this diagram is to remind that the identification method of emergency situations and the identification results given by the method are only a part of a system for the identification of emergency situations. Possibly the greatest influence on the correctness of the identification results is related to the measurement results 9 available, as well as the number of the measurement transducers 5 and their correct location. Also important for the identification result is correct modelling of the event being examined and the selection of correct features on the basis of the model developed for the purpose. Modelling in this context does not necessarily require developing any exact mathematical model, but rather, forming an intuitive concept of a method suited to the computation of the features. An example of such modelling is to consider anesthesia as a process in which the values stay stable in a normal situation and change in emergency situations as well as, e.g., at changing the settings of the anesthesia unit. On the basis of the above exemplary model, a solution was selected here in which the cause of the emergency situation is identified on the basis of changes occurring in the measurement results.

Though the identification method depicted in the diagram can be any of those used in the art, the term "pattern vector" is most commonly associated with pattern recognition and artificial neural networks, that is, with methods in which the pattern vector is generally examined as a whole. Because the identification process can also be earned out through examining the pattern vector feature by feature; the present method for emergency situation identification can equally well be based on, e.g., limit alarms, whereby the cause or causes of the emergency situation cannot be identified at all (identification accuracy 0%).

The good initial conditions furnished by correct placement of correct type transducers 5 and correct features for identification of emergency situations can easily be wasted by the use of an incorrect identification method, while moreover, unfavorable preconditions traceable to incorrect placement of transducers measuring incorrect variables and selection of incorrect features are difficult to compensate even by means of the most accurate identification method available. Therefore, replacing a good identification method with a still better one does not necessarily contribute essentially to the accuracy of the identification process, but rather, after exceeding a certain performance level, other properties of the identification method become more crucial: namely, such properties that are the particular object of the present invention making it different from, e.g., expert systems and the invention disclosed by Westenskow.

Accordingly, the present invention is related to the identification method employed at the highest level depicted in the diagram, as well as partially to the features used by the model and to the intuitive model providing the computational basis for extracting the features.

Figure 2:
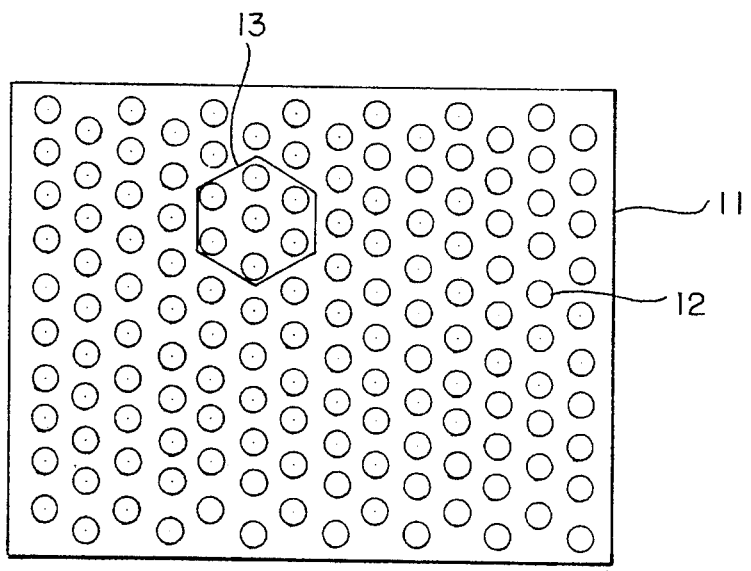
FIG. 2 is a diagrammatic presentation of a two-dimensional self-organizing map in which the map cells are located in a hexagonal lattice.

With reference to FIG. 2, a two-dimensional map 11 is shown having the map cells 12 organized into a hexagonal lattice 13, whereby each map cell is surrounded by six adjacent neighbors with the exception of the map cells at the borders of the map.

Figure 3:
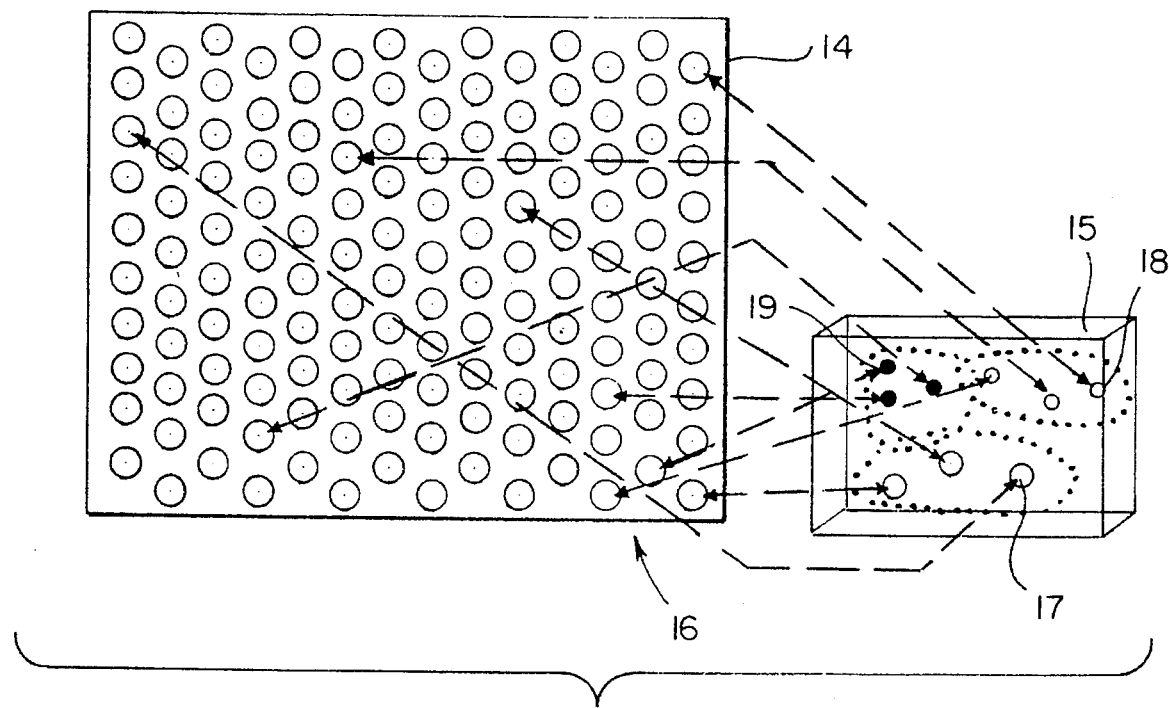
FIG. 3 is a presentation of an unordered self-organizing map.

With reference to FIG. 3, an unorganized two-dimensional map is shown in which the weight vectors and the pattern vectors to be identified are three-dimensional. Particularly, the components of pattern vectors are the different features computed from the measurement results obtained from the anesthesia system. The legend of reference numerals in the diagram is given below:

14 Two-dimensional self-organizing map

15 Weight vector/pattern vector space

16 Arrow indicating the map cell with which the weight vector is associated

17 Part of pattern vector space corresponding to emergency situation A

18 Part of pattern vector space corresponding to emergency situation B

19 Part of pattern vector space corresponding to emergency situation C

In the diagram the map is shown not yet having learned the ordered structure of the pattern vector space, whereby map cells corresponding to the same emergency situation are still dispersed to different pans of the map. Typically, the map is in the illustrated state prior to the training phase.

Figure 4:
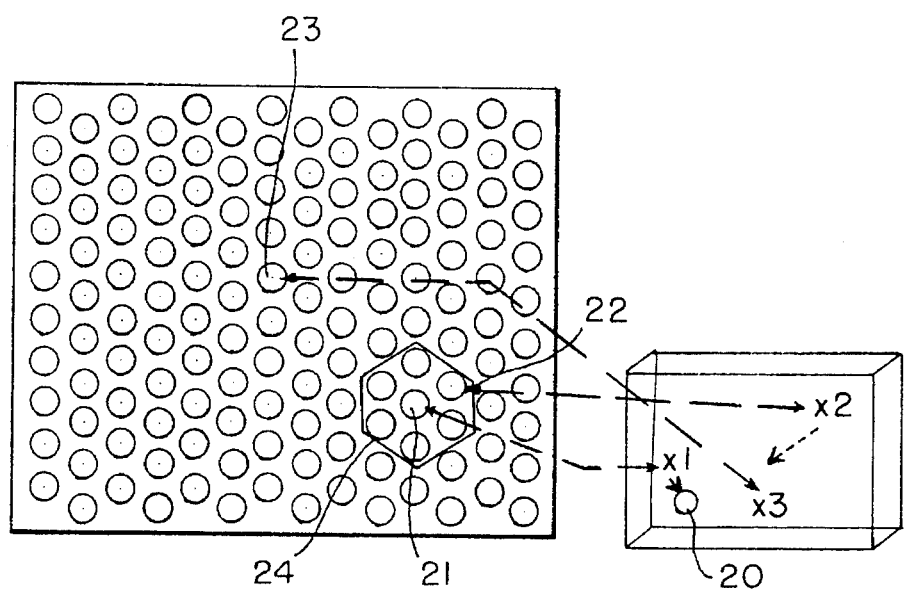
FIG. 4 is a presentation of the ordering process of the self-organizing map.

With reference to FIG. 4, the operation of the map is shown during the training phase. The legend of reference numerals in the diagram is given below:

Pattern vector to be taught to the map, whereby the vector comprises the above-mentioned features. The dimensionality of the pattern vector in this simple example is three, and the features can in an idealized case be considered comprising floating-point values which, when necessary, can be approximated by integers used in, e.g., computers. In context with anesthesia, the pattern vector can be considered comprising, e.g., the following components:
1. Expiratory air $CO_2$ content
2. Inspiratory tidal volume
3. Maximum flow rate of gas mixture into patient Winner cell having its corresponding weight vector denoted by x1. The winner cell is located closest to the pattern vector being taught to the map, and the distance between the two vectors can be expressed using, e.g., the normal Euclidian distance.

Generally, the size of neighborhood set of for the cell at the start of the training phase is almost as large as the entire map being trained. In this exemplifying diagram the training phase is shown progressed to a stage where the size of the neighborhood set 24 is already as small as 1. Also the weight vectors of cells included in the neighborhood set of the winner cell 21 are shifted closer to the pattern vector being trained. Accordingly, in this example the weight vector x2 associated with, e.g., map cell 22, is shifted closer to the pattern vector.

Map cell having its associated weight vector x3 located close to the pattern vector being taught to the map; this weight vector is not, however, shifted toward the pattern vector during the training phase as the map cell associated with it is not located within the neighborhood set of the winner cell.

Neighborhood set of winner cell, radius of the set is 1.

Figure 5:
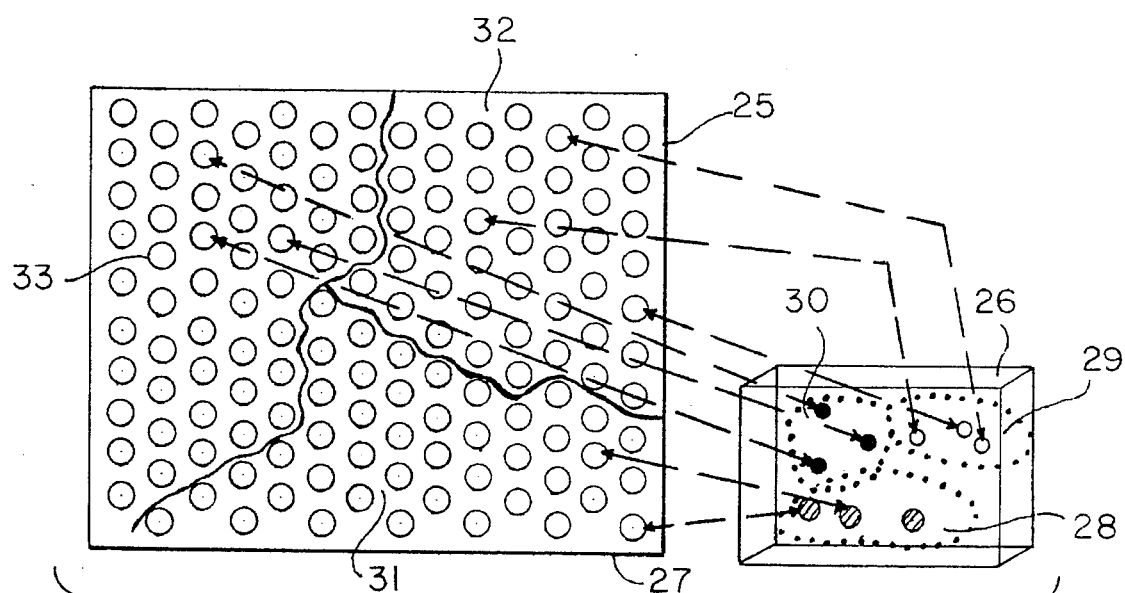
FIG. 5 is a presentation of the ready ordered self-organizing map.

With reference to FIG. 5, an organized map attained as the result of the above-described training phase is shown having each contiguous part of the vector space corresponding to each classified emergency situation represented by a continuous region on the map (in an ideal ease). The legend of reference numerals in the diagram is given below:

25 Two-dimensional self-organizing map

26 Weight vector/pattern vector space

27 Arrow indicating the map cell with which the weight vector is associated

28 Part of pattern vector space corresponding to emergency situation A

29 Part of pattern vector space corresponding to emergency situation B

30 Part of pattern vector space corresponding to emergency situation C

31 Map region corresponding to emergency situation A

32 Map region corresponding to emergency situation B

33 Map region corresponding to emergency situation C

Figure 6:
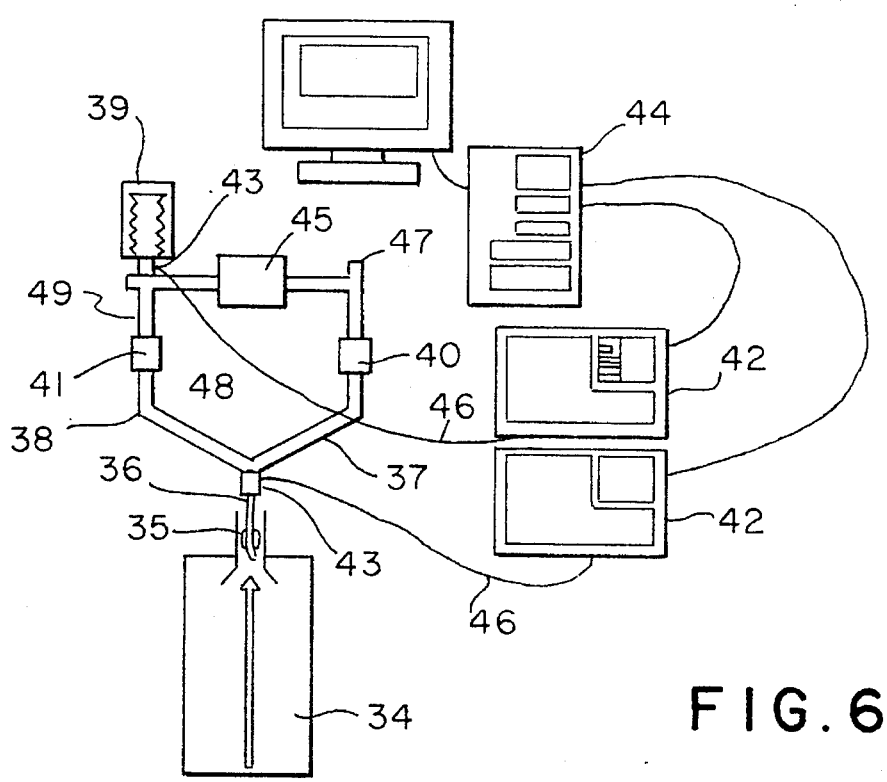
FIG. 6 is a diagrammatic layout of an anesthesia unit in which the invention according to the present patent application has been tested for its major parts.

With reference to FIG. 6, the breathing circuit of an anesthesia unit is shown in which the principal characteristics of the method according to the invention for recognizing and identifying emergency situations has been tested. The anesthesia unit used herein is Datex Flexima of the type having a semiclosed circulating breathing circuit. The measurement results were collected from two measurement points 10, of which one was located below the ventilator bellows and the other in connection with the intubation tube placed in the patient's thorax. The pattern vectors being trained and identified comprised features computed from the pressure, volume, flow, $CO_2$ content and oxygen content values of the gases inspired by the patient. The emergency situations to be identified comprised different kinds of breathing circuit obstructions and leaks and detachments of the gas sampling lines.

During the collection of samples related to emergency situations, the patient was replaced by a mechanical breathing simulator 34 into which nitrogen and carbon dioxide was taken to simulate oxygen consumption and $CO_2$ production. Most of the emergency situations generated by means of the simulated test material were recognized with an accuracy of greater than 90%, and this result can be considered satisfactory when compared with the identification accuracies of the same order of magnitude obtained in the an by means of expert systems and the invention disclosed by Westenskow.

The legend of reference numerals in the diagram is given below:

34 Mechanical respiration simulator (MII Model 1600)

35 Intubation tube cuff

36 Intubation tube

37 Inspiratory hose

Figure 7:
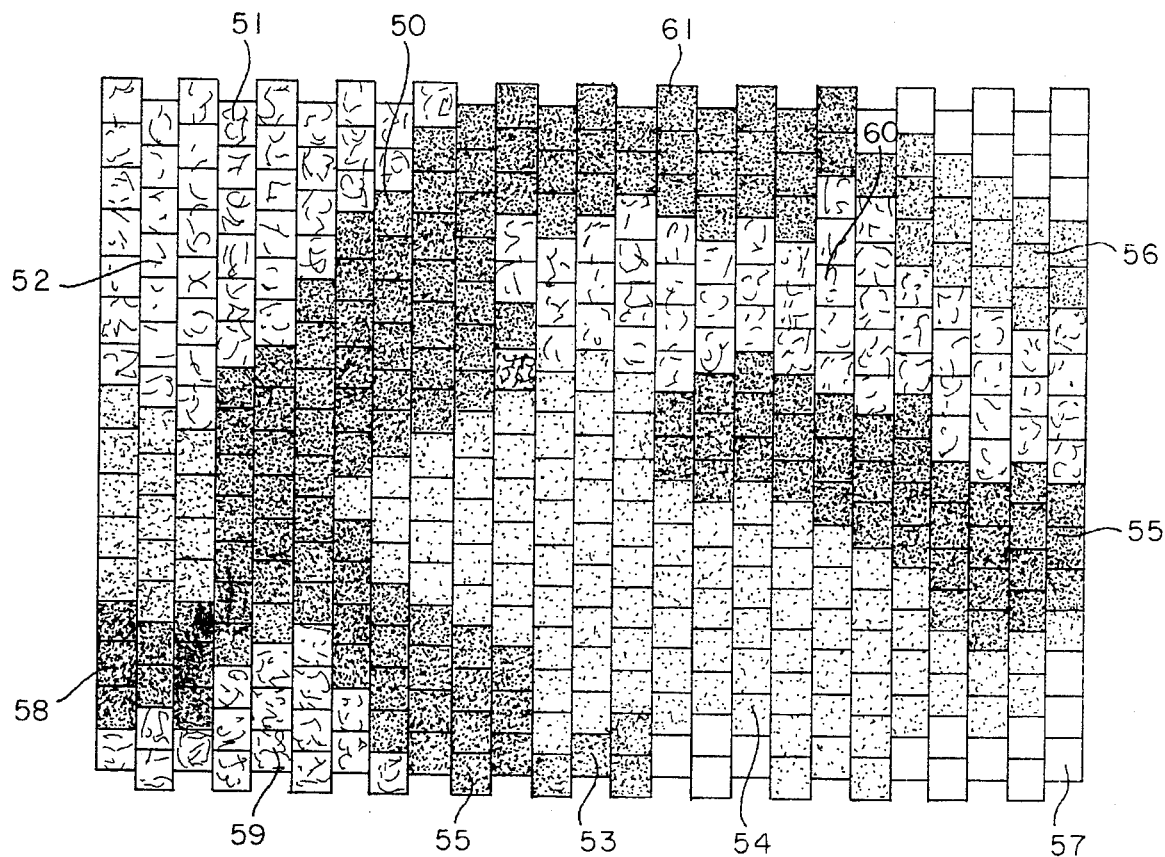
FIG. 7 is a presentation of the winner cell on one of the second level maps during a temporary obstruction of the intubation tube in the identification process of the fault events of the breathing circuit.

38 Expiratory hose
39 Bellows
40 Inspiratory valve
41 Expiratory valve
42 Gas monitor (Datex Capnomac Ultima)
43 Gas transducer (Dlite)
44 PC
45 $CO_2$ absorber canister
46 Gas sampling line
47 Fresh gas flow
48 Y-adapter
49 Expiratory valve socket With reference to FIG. 7, the map capable of identifying the cause of the malfunction situation (that is, cause of emergency situation) is shown; the map was generated during the above-described test of the method. The different intensities of gray levels depict the different emergency situations, and the regions associated with the different emergency situations are also denoted on the map by reference numerals. As the diagram is a gray-tone representation of an originally color-coded map, the gray-tone visualization of the regions related to different emergency situations may herein be less than satisfactory, e.g., at the regions corresponding to the intubation tube obstruction and the expiration air hose obstruction, respectively.

Figure 8:
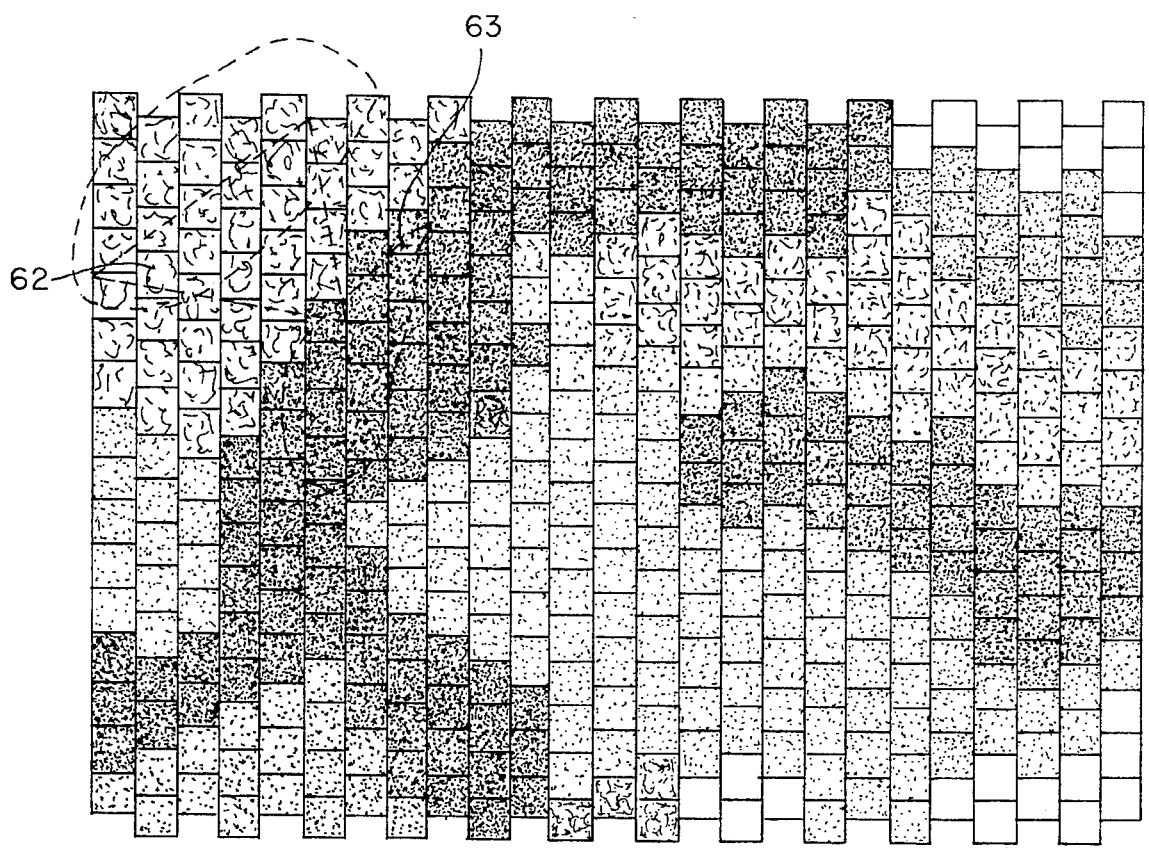
FIG. 8 is a presentation of the winner cell movement on one second level map during a transient obstruction of the intubation tube in the identification process of the fault events of the breathing circuit.

The legend of reference numerals in the diagram is given below:

50 Map region corresponding to a normal situation
51 Expiratory hose obstruction
52 Intubatory tube obstruction
53 Gas transducer obstruction (Dlite)
54 Expiratory hose/Y-adapter/Expiratory valve socket leak
55 Inspiratoryr hose leak
56 Detachment of $CO_2$ sampling line
57 Detachment of pressure/flow sampling line
58 Inspiratory valve flap leak
59 Expiratory valve flap leak
60 Bypass leak of intubaion tube cuff
61 Inspiratory hose obstruction With reference to FIG. 8, the movement of the winner cell via the region corresponding to the expiratory hose obstruction to the region 63 corresponding to the intubation tube obstruction, and therefrom further to the normal situation region 62 when a transient obstruction of the intubation tube occurs.

Figure 9:
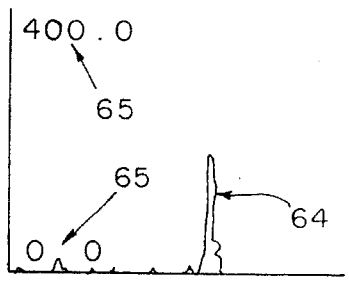
FIG. 9 is the quantization error graph of the emergency identification map during a temporary clogging of the intubation tube.

With reference to FIG. 9, a significant increase of quantization error owing to an intubation tube obstruction 64 is shown on the emergency situation identifying map. Numerical values 65 plotted on the Y-axis depict the magnitude of the quantization error.

Figure 10:
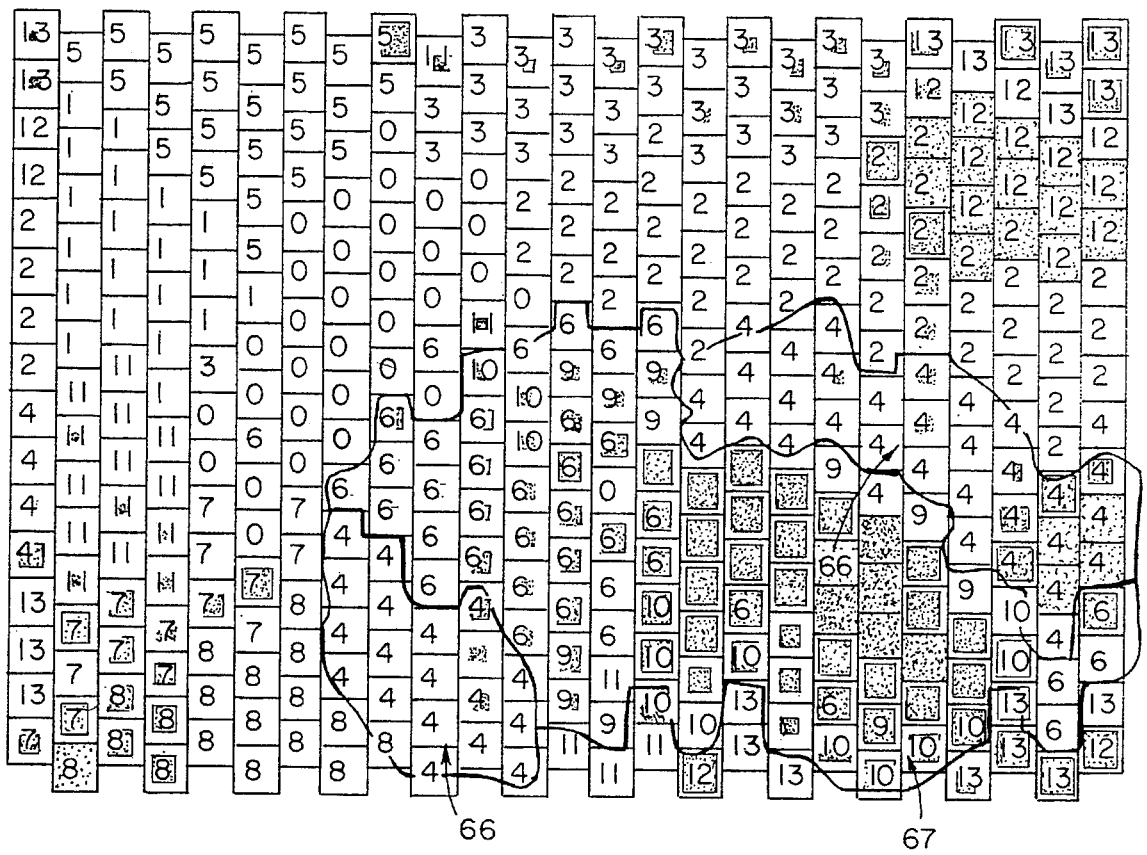
FIG. 10 is a plot of the values of the emergency-identifying feature at different parts of the map.

With reference to FIG. 10, the method by which the map differentiates an respiration hose leak 66 from an expiration air hose/Y-adapter/expiration air valve socket leak 67 is shown. The diagram illustrates the change of the absolute value of the $CO_2$ content minimum level during the breathing cycle. Denoted by a darker gray tone on the diagram are those regions whose cells are associated with a weight vector having the above-mentioned feature values above normal, and respectively, by a lighter gray tone those regions whose cells are associated with a weight vector having the above-mentioned feature values below normal. The larger the size of the square drawn into the cell on the map, the more the feature deviates from the normal value.

The diagram makes it easy to understand that it is particularly the value of the examined feature that differentiates the above-discussed emergency situations from each other when the map performs the identification of emergency situations. By virtue of examining the weight vectors by component in the different regions of the map and comparing the values of said components to the emergency situations associated with corresponding map cells, the operator can readily resolve how the map identifies the emergency situations.

Figure 11:
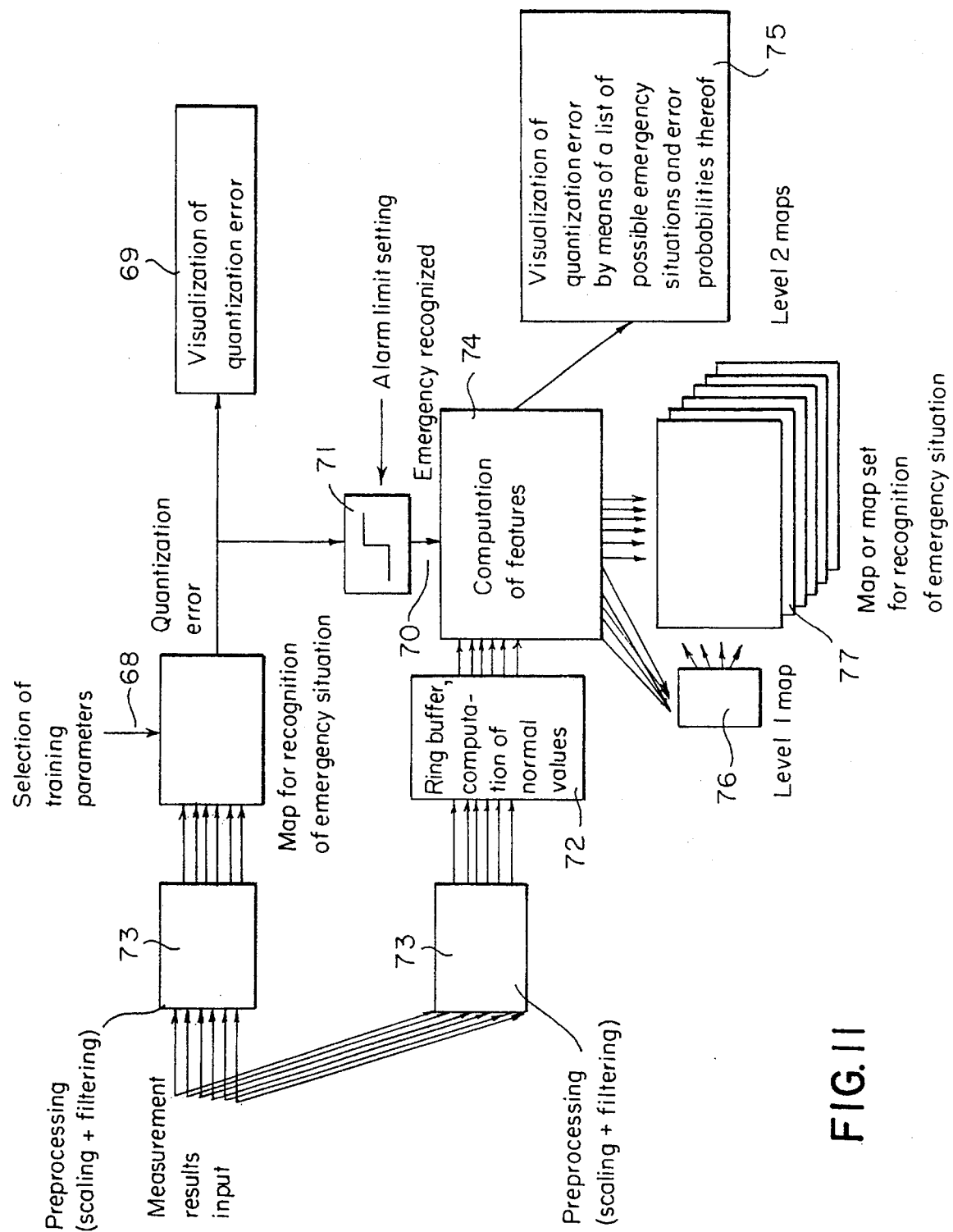
FIG. 11 is a functional block diagram of the method in practical use.

With reference to FIG. 11, the practical operation of the method for identifying emergency situations is illustrated after level 1 map 76 and level 2 map 77 have been trained by means of training material collected using a breathing simulator or test animals. First, the level 1 map is trained with the help of absolute pattern vectors associated with normal situations, said vectors being, as described in the text above, formed using measurement results of discrete instants of time alone. The map set capable of identifying emergency situations is trained by a map at a time comprising adjusting the anesthesia system so that the absolute pattern vectors computed from the measurement results are located closer to that weight vector of the level 1 map cell associated with the level 2 map being trained than any other weight vector of the level 1 map. After this, samples associated with each emergency situation being examined are collected by virtue of foxing the pattern vectors through comparison of the measurement results with normal values and then training the pattern vectors to the map.

The training of a self-organizing map is exhaustively described in the literature, whereby its closer examination can in this context be omitted.

The map or map set capable of identifying an emergency situation is trained during actual anesthesia deliveries. The user has the option of retraining the emergency situation identifying map if the anesthesia unit is, e.g., moved to a new, entirely different operating environment. The user can also define a sufficiently narrow fixed range for the parameter values used in training the map, whereby the map can be used in a continuously adaptive mode. The wide selection of details and possibilities available in training the emergency situation identifying map are denoted in the diagram by reference numeral 68, "Selection of training parameters".

Reference numeral 69 in the diagram refers to the quantization error of the emergency identifying map, and if the quantization error exceeds a level set by the user at the stage denoted by reference numeral 71, the emergency situation identifying system issues a signal 70. At this moment, the values of the change-associated features 74 required for identifying the emergency situation are determined by means of normal values stored in a ring buffer 72 and corresponding measurement values. The operating principle of the ring buffer 72 is as follows: 1) If the ring buffer is not full, the pattern vector is stored in the first free buffer location available. 2) If the ring buffer becomes full, the oldest value stored in the ring buffer is dumped at the storage of the new value. Prior to the storage into the ring buffer, the measurement results can be filtered and scaled in the unit denoted by reference numeral 73. Scaling removes the effect of disproportionality caused by the variance and different ranges of variation in measurement results: For example, the changes m tidal volume during an emergency situation can be hundreds of milliliters simultaneously as, e.g., the $CO_2$ content may increase by, e.g., only one percent unit.

It must be noted that part of the measurement results can be, e.g., signals related to the anesthesia unit adjustments. Because such anesthesia unit adjustments, for example, may corrupt the measurement results, the above-described arrangement can be used to automatically warn the user of the possibility that said adjustments may have affected the measurement results in the case the values stored in the ring buffer are found to include measurement results indicating changes of anesthesia unit adjustments.

After the absolute pattern vector corresponding to a given instant of time and the absolute pattern vector corresponding to a normal situation have been read from the ring buffer, the emergency situation identifying level 2 map is formed by finding the weight vector closest matching with absolute pattern vector of normal situation on the level 1 map. Subsequently, the location of the winner cell is plotted onto the level 2 map. Also the movement of the winner cell can be plotted on the map, e.g., in the manner explained for FIG. 7 above.

The invention disclosed in the present patent application is thus related to the use of the benefits of a prior-art method, namely the self-organizing map in a novel application in which the method has never been used before. The invention also combines a plurality of self-organizing maps in a novel manner to the end of improving the accuracy of emergency situation identification at changes of the anesthesia system operating point. The method is capable of identifying emergency situations in any anesthesia system. The only precondition for identification is the use of such measurement results and features computed from said results that are in principle applicable to the identification of emergency situations. The above-described examples of the system capable of identifying emergency situations in the use of an anesthesia unit are only exemplary and nonlimiting, whereby their illustration must not be understood to prohibit the use of the disclosed method for recognizing and identifying emergency situations in other anesthesia occasions.

We claim:

1. A method for recognizing and identifying emergency situations in an anesthesia system comprising:

a) measuring a plurality of variables associated with an anesthesia delivery to produce measurement values associated therewith, b) forming the measurement values of said measured variables into pattern vectors characterizing instantaneous states of the system, c) providing a emergency identifying self organizing map;

d) training the emergency identifying self organizing map, prior to an actual measurement situation, by providing reference material comprising pattern vectors corresponding to actual situations, the pattern vectors being arranged in said self organizing map as weight vectors, each weight vector representing a particular combination of system parameters representing an actual condition, and e) comparing the pattern vectors formed from the measurement results with weight vectors ($m_1$) of the emergency identifying self-organizing map to recognize and identify emergency situations.

2. A method as defined in claim 1, wherein the emergency identifying self organizing map of claim 1 is a single level self organizing map, said method being capable of concurrently identifying both the existence and cause of an emergency situation by means of level 1 and level 2 self-organizing maps, said step e) identifying the cause of the emergency situation defined by the closest weight vector in said level 1 self organizing map to the pattern vector corresponding to the current measurement values produced in said step b), each weight vector of the level 1 self organizing map being associated with one of a plurality of level 2 self organizing maps;

said method further including, f) utilizing the level 2 self organizing map corresponding to the weight vector in said level 1 self organizing map to further identify the cause of the emergency situation.

3. The method of claim 2 wherein said level 2 self organizing maps are also formed of a plurality of map elements each having a weight vector representing a particular combination of system parameters representing an actual condition.

4. The method of claim 3 wherein the level 2 self organizing map contains only weight vectors corresponding to weighing vectors arranged closer to one another on said level 1 self organizing map than other weighing vectors on said level 1 self organizing map.

5. The method of claim 4 where said level 2 self organizing map is trained after said level 1 self organizing map.

* * * * *